United States Patent [19]

Fujii et al.

[11] Patent Number: 4,563,527

[45] Date of Patent: Jan. 7, 1986

[54] AMIDINE COMPOUNDS

[75] Inventors: Setsuro Fujii, Toyonaka; Toyoo Nakayama, Funabashi; Shigeki Nunomura, Chiba; Kimio Sudo, Chiba; Shin-ichi Watanabe, Funabashi; Toshiyuki Okutome, Tokyo; Yojiro Sakurai, Kamakura; Masateru Kurumi, Narita; Takuo Aoyama, Sakura, all of Japan

[73] Assignee: Torii & Co., Ltd., Tokyo, Japan

[21] Appl. No.: 632,350

[22] Filed: Jul. 19, 1984

[51] Int. Cl.$^4$ ................ C07D 307/54; C07D 307/85; C07D 333/38
[52] U.S. Cl. .................... 546/169; 544/146; 544/152; 544/153; 544/376; 544/379; 546/196; 546/206; 546/269; 546/283; 546/284; 548/316; 549/68; 549/69; 549/71; 549/468; 549/480; 549/485
[58] Field of Search .............. 544/146, 152, 153, 376, 544/379; 546/196, 206, 169, 269, 283, 281; 548/316; 549/68, 69, 71, 468, 480, 485; 424/248.51, 248.54, 248.55, 250, 273 R, 275, 285

[56] References Cited

FOREIGN PATENT DOCUMENTS 2083818 3/1982 United Kingdom .

OTHER PUBLICATIONS

Hawley, The Condensed Chemical Dictionary, Van Nostrand Reinhold, New York (1977) p. 74.

Primary Examiner—Richard L. Raymond
Attorney, Agent, or Firm—Beveridge, DeGrandi & Weilacher

[57] ABSTRACT

Amidine compounds of the formula

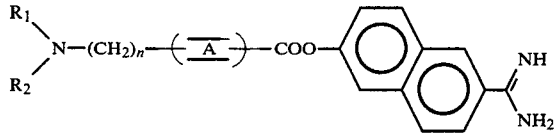

and pharmaceutically acceptable acid addition salts thereof are novel compounds and are useful as powerful anti-trypsin, anti-plasmin, anti-kallikrein and anti-thrombin agents. They are also useful as a powerful anti-complement agent.

6 Claims, No Drawings

AMIDINE COMPOUNDS

This invention relates to novel amidino compounds of formula (I)

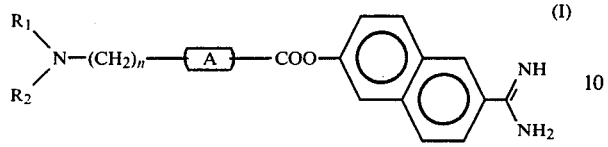

wherein A represents furan, thiophene or benzofuran; $R_1$ represents a hydrogen atom or a straight or branched chain alkyl group of 1 to 4 carbon atoms; $R_2$ represents a hydrogen atom, a straight or branched chain alkyl group of 1 to 4 carbon atoms, an acyl group or

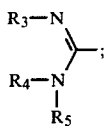

$R_3$, $R_4$ and $R_5$ represent a hydrogen atom or a straight or branched chain alkyl group of 1 to 4 carbon atoms; $R_1$ to $R_5$ taken together with the nitrogen atoms to which they are attached form a ring, which may optionally contain other hetero atoms; and n is 0, 1 or 2, and the pharmaceutically acceptable acid addition salts thereof.

In formula (I) $R_2$ is preferably

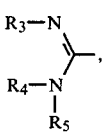

wherein $R_3$, $R_4$ and $R_5$ are as defined above.

In formula (I) the acyl group for $R_2$ is preferably $R_6$—CO—, wherein $R_6$ represents a straight or branched chain alkyl group of 1 to 15 carbon atoms, a straight or branched chain alkoxy group of 1 to 4 carbon atoms, benzyloxy,

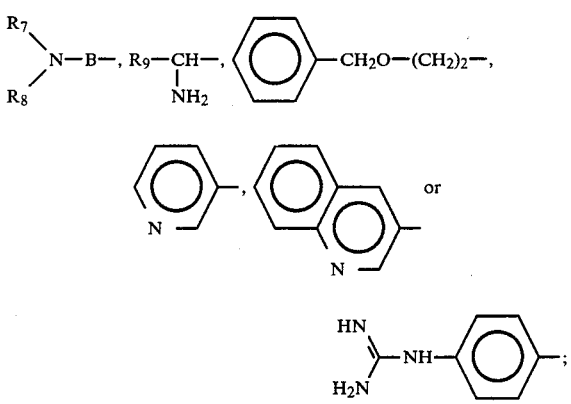

$R_7$ and $R_8$ represent a hydrogen atom, a straight or branched chain alkyl group of 1 to 4 carbon atoms or benzyloxycarbonyl; B represents —$(CH_2)_m$— or

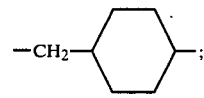

m is 1 or 2; and $R_9$ represents

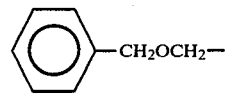

or $NH_2$—$(CH_2)_4$—.

In formula (I) A is preferably furan.

An object of this invention is to provide a pharmaceutically useful novel amidino compounds and pharmaceutically acceptable acid addition salts thereof.

Another object of this invention is to provide a process for producing said novel amidino compounds.

Still another object of this invention is to provide powerful anti-trypsin, anti-plasmin, anti-kallikrein and anti-thrombin agents.

A further object of this invention is to provide powerful anti-complement agents.

The compound (I) of this invention can be produced by the reaction between a carboxylic acid compound of formula (II) or a reactive intermediate thereof and 6-amidino-2-naphthol of formula (III) or preferably an acid addition salt thereof.

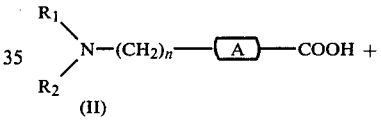

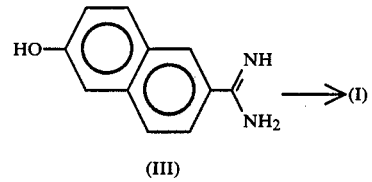

$R_1$, $R_2$, A and n are as defined above. The reactive intermediates, as herein referred to, include acid halides and acid anhydrides commonly used in the dehydration condensation and the reactive intermediates formed by reacting dicyclohexyl carbodiimide (DCC), diphenyl phosphorylazide (DPPA), or the like with a carboxylic acid derivative.

The process for producing the present compound is described below in detail.

The present compound (I) can be prepared by dissolving or suspending a carboxylic acid compound (II) in an organic solvent such as dimethylformamide, pyridine, or the like, then allowing the compound (II) to react with an carboxylic acid activator such as dicyclohexylcarbodiimide (DCC), diphenylphosphoryl azide (DPPA), or the like, which is usually used as dehydration-condensation agent, and adding 6-amidino-2-naphthol (III) or preferably an acid addition salt thereof to the reaction product.

For instance, when DCC is used as the dehydration-condensation agent, a carboxylic acid derivative (II) is added to a solvent such as pyridine, then 6-amidino-2- naphthol (III) is added, and the mixture is stirred at a temperature between −30° and 80° C., preferably at room temperature, for 3 to 5 hours to complete the reaction, though it is not objectionable to continue the reaction overnight. Dicyclohexylurea (DCU) precipitates out of the reaction mixture, while the present compound (I) either precipitates with DCU or remains dissolved in the solvent. In the former case, both precipitates are collected by filtration, then suspended in a suitable solvent such as dimethylformamide or the like and the mixture is filtered to remove insoluble DCU. After adding to the filtrate a solvent such as ethyl ether, ethyl acetate, acetone or the like, the precipitate is collected by filtration to obtain the present compound (I). Alternatively, the combined precipitate of DCU and the present compound (I) is collected by filtration, then added to a suitable solvent such as dimethylformamide, water or the like to remove insoluble DCU by filtration, the filtrate is added to a saturated aqueous sodium hydrogencarbonate solution to obtain the present compound (I) in the form of carbonate. In the latter case, where the present compound remains dissolved in the reaction mixture, DCU is removed by filtration and the filtrate is admixed with a solvent such as ethyl ether, acetone, ethyl acetate, or the like to obtain the present compound (I).

In another process, when it is intended to use an acid halide a a reactive intermediate of a carboxylic acid derivative (II), the latter deviative (II) is allowed to react with an acid halogenation agent such as $SOCl_2$, $SOBr_2$, $PCl_5$ or the like to synthesize an acid halide represented by formula (IV)

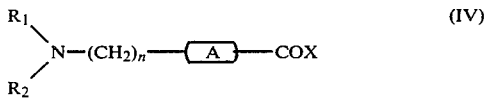

(IV)

wherein $R_1$, $R_2$, A and n are as defined above and X represents a halogen atom. The acid halide is added to a solution of 6-amidino-2-naphthol (III), preferably in the form of an acid addition salt, dissolved in dimethylformamide, pyridine, dimethyl sulfoxide or the like and allows to react in the presence of a dehydrohalogenation agent. The dehydrohalogenation agents which can be used include inorganic bases such as potassium carbonate, sodium carbonate, sodium hydroxide and the like and organic bases such as triethylamine, pyridine, dimethylaniline and the like. Of these bases, pyridine is preferred. Although the reaction proceeds readily at a temperature in the range of −30° to 80° C., it is preferable for the purpose of avoiding side reaction to conduct the reaction in the early stage under ice cooling and then at room temperature. The reaction is complete in 2 to 5 hours, though the reaction mixture can be left overnight. After completion of the reaction, the reaction mixture is treated in a customary manner. For instance, when pyridine was used as the reaction medium, a solvent such as ethyl ether or ethyl acetate is added to the reaction mixture to precipitate a solid reaction product which is then recrystallized from a suitable solvent such as a methanol-ethyl ether mixture to obtain the present compound (I).

The compound (III) is replaced by the corresponding compound wherein an amidino group is protected, and the latter compound can be allowed to react with the compound (II) to obtain the compound (I) wherein the amidino group is protected. Splitting off an amidino protecting group by a usual manner can yield the present compound (I).

The amidino protecting group may be conventionally used ones. Examples thereof include a benzyloxycarbonyl or t-butoxycarbonyl group. Examples of a method for splitting off an amidino protecting group include a reductive elimination by palladium-carbon or an elimination by trifluoroacetic acid or HBr/acetic acid.

Further, if desired, the present compound (I) can be prepared in the corresponding reduced form by the reduction of a suitable compound of formula (I) by use of a suitable reducing agent. For example, a compound of formula (I) having a nitro group is converted into a compound of formula (I) having an amino group by the reduction.

Still further, if desired, the present compound can be obtained by the removal of protective group of amino. The protective groups, as herein referred to, include those which are commonly used, such as, for example, benzyloxycarbonyl, tert-butoxycarbonyl, benzyl and tert-butyl groups. For instance, a compound having an aminomethyl group is obtained by the removal of the protective group from a compound having a benzyloxycarbonylaminomethyl group.

If necessary, acid addition salts of the present compound may be prepared in a customary manner. For instance, carbonate of the present compound is dissolved or suspended in a solvent such as methanol, DMF or the like and the carbonate is allowed to dissolve by the addition of an acid such as methanesulfonic acid, hydrochloric acid or the like. To the resulting solution is added a solvent such as ethyl ether, ethyl acetate or the like to obtain a corresponding acid addition salt. Acids which can be used are pharmaceutically acceptable ones including inorganic acids such as hydrochloric acid, sulfuric acid and phosphoric acid and organic acids such as acetic acid, lactic acid, citric acid, methanesulfonic acid, succinic acid, fumaric acid and maleic acid.

The present compound and the pharmaceutically acceptable acid addition salt thereof possess powerful inhibitory activities against proteases, that is, trypsin, plasmin, kallikrein and thrombin and are effective as an anti-trypsin agent for the treatment of pancreatitis, as an anti-plasmin or anti-kallikrein agent for hemorrhagic diseases, and as an anti-thrombin agent for thrombus.

With respect to the above-mentioned proteases, their roles in a living body, the relationship to the diseases, the clinical significance of these proteases inhibitors and the significance of the tests herein performed are explained below:

I. Trypsin: Trypsin is a protease existing originally in the form of proenzyme trypsinogen in the pancreas and the proenzyme is secreted into the small intestine where it is transformed into trypsin by activation with enterokinase existing therein. Trypsin has a role as one of digestive enzymes. If the trypsinogen is activated by any chance in the pancreas to form trypsin, the pancreas tissue will be injured to manifest clinically the symptoms of pancreatitis. In fact, it is known that in an experiment using rat as test animal, when trypsin is injected conversely into the pancreas, the onset of intense pancreatitis is observed but the disease is cured by the administration of a trypsin inhibitor. From this fact, it is presumable that the present compound having a strong trypsin inhibitory activity is useful as an antitrypsin agent which is clinically effective for the treatment of pancreatitis.

II. Plasmin: Plasmin is an enzyme existing in the blood, usually in the form of proenzyme plasminogen which is converted to plasmin by the activation with a plasminogen tissue activator such as urokinase. This enzyme acts reversely to the action of thrombin, that is, it acts to dissolve fibrin. For this reason, plasmin plays an important role in securing blood flow through capillaries. However, when this enzyme becomes abnormally activated for some reason, it causes hemorrhagic diseases. This enzyme participates also in inflammation, increasing the vascular permeability and causing edema or the like. Therefore, an inhibitor for this enzyme is useful as a drug to test hemorrhagic diseases and inflammation.

III. Kallikrein: Kallikrein is an enzyme widely distributed in blood and other organs and glands, usually in the form of its precursor prekallikrein which is activated with Hageman factor or other proteases. This enzyme participates in the hypotensive kallikrein-kinin system which counteracts the hypertensive renin-angiotensin system and plays an important role in the control of blood pressure. This enzyme participates also in exogenous coagulation system. Further, kallikrein originated from organs or glands plays an important role in the improvement of local circulation. However, an abnormal activation, particularly an abnormal local activation, of this enzyme causes an insufficiency of local circulation due to the exaggeration of coagulation system, causing inflammation, ulcer, or the like. Therefore, a kallikrein inhibitor is useful for the control of blood pressure and as a drug for the treatment of inflammation or ulcer.

IV. Thrombin: Thrombin is known as an enzyme having a blood coagulating activity. In normal state, thrombin is formed by the activation of prothombin in the blood when the vascular wall is injured. Thrombin acts to decompose the fibrinogen in the blood into fibrin. The resulting fibrin deposits on the injured part of vascular wall to prevent plasma components from transudation and simultaneously to promote the restoration of tissues. However, when the coagulation system is abnormally activated for some reason, a large number of fine thrombi are formed in capillaries throughout the entire body. Therefore, the present compound is useful as a drug for the treatment of such a disease.

The present compound and its pharmaceutically acceptable acid addition salts possess a strong C1 esterase ($\overline{\text{C1r}}$, $\overline{\text{C1s}}$) inhibitory activity, an ability of inhibiting the complement mediated hemolysis, and a therapeutic activity against the Forssman shock in which the activation of the complement system caused by an immune complex is said to play an important role. This indicates that the present compound is useful as an anti-complement agent effective for the treatment of allergic diseases such as nephritis associated with the complement.

The role of complement in the living body, the interrelation between a disease and the complement, the clinical significance of inhibitor, and the significance of tests (inhibition of $\overline{\text{C1r}}$, $\overline{\text{C1s}}$, complement mediated hemolysis, and Forssman shock) performed by the present inventors are described below.

Anti-complement activity:

(1) $\overline{\text{C1r}}$, $\overline{\text{C1s}}$

The complement is one of the serum components and comprises 9 components of C1 to C9. C1 is separated into 3 subcomponents of C1q, $\overline{\text{C1r}}$ and $\overline{\text{C1s}}$. $\overline{\text{C1s}}$ and $\overline{\text{C1r}}$ mean activated C1s and activated C1r, respectively. The complement was thought at first to perform a part of the infection protective process of living body, since it shows bacteriolysis, but recently an intimate relation to the immunity has been evident. It was shown that the complement is activated by the immune complex progressively from C1 to C9 and exhibits cytolysis or hemolysis at the final stage (activation of C9). It was also disclosed that the fragments (e.g. C3a, C5a) liberated in the course of activation of the complement system exaggerate the vascular permeability and promote the chemotaxis of polymorphonuclear leucocytes or immune adherence. Since that time, the interrelationship between the abnormal activation of complement and various diseases, particularly immune diseases, has been extensively investigated and, as the result, the intimate association of autoimmune diseases with the complement is beginning to be disclosed. Examples of autoimmune diseases caused by the abnormal activation of complement include autoimmune hemolytic anemia, autoimmune thrombocytopenia, leukopenia, glomerulonephritis, systemic lupus erythematosus, serum sickness and periarteritis nodosa. It is expectable to cure such diseases by inhibiting the activation of complement or inhibiting the activated complement in an early stage. The present inventors examined the C1 esterase inhibitory effect of the present compound by using C1 esterase as target enzyme and, in addition, the influence of the present compound on the complement system to estimate the usefulness of the present compound as a drug for the treatment of autoimmune diseases.

(2) Complement mediated hemolysis

The complement mediated hemolysis is widely used as a means to determine the titration of complement. The principle of this method is based on the fact that hemolysis is caused by the activation of complement, when the latter is added to a complex (immune complex) of erythrocytes and the antibody thereof. The degree of hemolysis varies in proportion to the amount of complement added. Therefore, when a known amount of complement admixed with a C1 esterase inhibitor is used, the hemolysis must be suppressed in proportion to the inhibitory activity. The present compound having C1 esterase inhibitory activity showed strong inhibition of complement mediated hemolysis as shown hereinafter.

(3) Forssman shock

Quite different from other animals, guinea pig has on the surface of its organs a specific antigen called Forssman antigen which specifically reacts with the antibody of sheep erythrocyte. Forssman shock is based on the above principle and is a shock caused by the administration of antibody of sheep erythrocyte to a guinea pig. The Forssman shock was investigated in detail by many researches and it was definitely shown that this shock is a model case where the complement plays the principal part and that the shock is associated with a classical pathway in which the complement system is activated progressively starting from C1. Since the participation of complement in autoimmune diseases has been established, the Forssman shock can be said to be useful means for testing a drug for autoimmune diseases. A drug effective for the treatment of Forssman shock is useful as a drug of autoimmune diseases.

[Anti-trypsin, anti-plasmin, anti-kallikrein and anti-thrombin activities]

The anti-trypsin, anti-plasmin, anti-kallikrein and anti-thrombin activities were determined according to the method of Muramatsu et al. [M. Muramatus, T. Onishi, S. Makino, Y. Hayashi and S. Fujii, J. of Biochem., 58, 214 (1965)]. The results were as shown in Table 1. The data summarized in Table 1 are expressed in terms of molar concentration ($ID_{50}$) of the test compound which inhibits 50% of the activity of each enzyme to hydrolyze TAME (tosylalginine methyl ester). The compound No. corresponds to the compound number shown in Examples. The figure in parentheses shows the percentage inhibition at a concentration of the compound of $1 \times 10^{-5}M$.

TABLE 1

| Compound No. | Trypsin | Plasmin | Kallikrein | Thrombin |
|---|---|---|---|---|
| 1 | (35) | (15) | $5 \times 10^{-6}$ | (22) |
| 2 | $2 \times 10^{-6}$ | $8 \times 10^{-7}$ | $3 \times 10{-7}$ | $9 \times 10^{-7}$ |
| 3 | $1 \times 10^{-7}$ | $5 \times 10^{-7}$ | $9 \times 10^{-7}$ | $3 \times 10^{-7}$ |
| 4 | $4 \times 10^{-6}$ | (42) | $6 \times 10^{-6}$ | $8 \times 10^{-6}$ |
| 5 | $3 \times 10^{-7}$ | $5 \times 10^{-7}$ | $5 \times 10^{-7}$ | $2 \times 10^{-7}$ |
| 6 | $4 \times 10^{-6}$ | $3 \times 10^{-6}$ | $4 \times 10^{-7}$ | $2 \times 10^{-6}$ |
| 7 | $2 \times 10^{-6}$ | $7 \times 10^{-7}$ | $4 \times 10^{-7}$ | $2 \times 10^{-6}$ |
| 8 | $2 \times 10^{-6}$ | $8 \times 10^{-7}$ | $4 \times 10^{-7}$ | $1 \times 10^{-6}$ |
| 9 | $9 \times 10^{-7}$ | $6 \times 10^{-6}$ | (47) | $1 \times 10^{-6}$ |
| 10 | $4 \times 10^{-8}$ | $3 \times 10^{-6}$ | $4 \times 10^{-7}$ | $2 \times 10^{-7}$ |
| 11 | $3 \times 10^{-6}$ | $2 \times 10^{-6}$ | $4 \times 10^{-7}$ | $4 \times 10^{-7}$ |
| 12 | $3 \times 10^{-7}$ | $4 \times 10^{-7}$ | $3 \times 10^{-7}$ | $5 \times 10^{-7}$ |
| 14 | $1 \times 10^{-6}$ | $2 \times 10^{-6}$ | $5 \times 10^{-7}$ | $7 \times 10^{-7}$ |
| 15 | $2 \times 10^{-7}$ | $3 \times 10^{-7}$ | $4 \times 10^{-7}$ | $6 \times 10^{-7}$ |
| 16 | $1 \times 10^{-6}$ | $1 \times 10^{-7}$ | $4 \times 10^{-7}$ | $4 \times 10^{-7}$ |
| 17 | $8 \times 10^{-7}$ | $2 \times 10^{-6}$ | $1 \times 10^{-6}$ | $7 \times 10^{-7}$ |
| 18 | $9 \times 10^{-7}$ | $5 \times 10^{-7}$ | $5 \times 10^{-7}$ | $5 \times 10^{-7}$ |
| 19 | $2 \times 10^{-7}$ | $3 \times 10^{-7}$ | $7 \times 10^{-7}$ | $2 \times 10^{-7}$ |
| 23 | $5 \times 10^{-7}$ | $2 \times 10^{-6}$ | $3 \times 10^{-6}$ | $4 \times 10^{-6}$ |
| 25 | $7 \times 10^{-7}$ | $6 \times 10^{-7}$ | $2 \times 10^{-6}$ | $3 \times 10^{-6}$ |
| 26 | $3 \times 10^{-7}$ | $6 \times 10^{-7}$ | $3 \times 10^{-6}$ | $2 \times 10^{-6}$ |
| 28 | $4 \times 10^{-6}$ | $9 \times 10^{-6}$ | $4 \times 10^{-6}$ | (46) |
| 31 | $2 \times 10^{-8}$ | $4 \times 10^{-7}$ | $4 \times 10^{-7}$ | $1 \times 10^{-6}$ |
| 33 | $5 \times 10^{-7}$ | $4 \times 10^{-7}$ | $4 \times 10^{-6}$ | $3 \times 10^{-6}$ |
| 34 | $6 \times 10^{-7}$ | $2 \times 10^{-6}$ | $3 \times 10^{-7}$ | $5 \times 10^{-7}$ |
| 35 | $8 \times 10^{-6}$ | $3 \times 10^{-6}$ | $9 \times 10^{-7}$ | $3 \times 10^{-6}$ |
| 36 | $2 \times 10^{-7}$ | $6 \times 10^{-7}$ | $6 \times 10^{-7}$ | $3 \times 10^{-7}$ |
| 37 | $7 \times 10^{-7}$ | $4 \times 10^{-7}$ | $4 \times 10^{-7}$ | $9 \times 10^{-7}$ |
| 38 | $5 \times 10^{-7}$ | $4 \times 10^{-7}$ | $3 \times 10^{-7}$ | $8 \times 10^{-8}$ |
| 39 | $8 \times 10^{-7}$ | $4 \times 10^{-7}$ | $5 \times 10^{-7}$ | $2 \times 10^{-6}$ |

[Anti-complement activity]

(1) Anti-C1 ($C\bar{1}r$, $C\bar{1}s$) activity and inhibition of complement mediated hemolysis:

The anti-C1 esterase ($C\bar{1}r$, $C\bar{1}s$) activity was determined according to the method of Okamura et al. [K. Okamura, M. Muramatsu and B. Fujii, Biochem. Biophys. Acta, 295, 252–257 (1973)]. The inhibition of complement mediated hemolysis was determined according to the method of Baker et al. [B. R. Baker and E. H. Erickson, J. Med. Chem. 12, 408–414 (1969)]. The results obtained were as shown in Table 2. The figures in Table 2 have the following meanings:

$C\bar{1}r$: Molar concentration of the test compound which inhibits 50% of the ability of $C\bar{1}r$ to hydrolyse AAME (acetylarginin methyl ester) ($ID_{50}$).

$C\bar{1}s$: Molar concentration of the test compound which inhibits 50% of the ability of $C\bar{1}s$ to hydrolyse ATEE (acetyltyrosin ethyl ester) ($ID_{50}$).

The figure in parentheses shows the percent inhibition at a concentration of the compound of $1 \times 10^{-5}M$.

Inhibition of complement mediated hemolysis (%)

The inhibitory activity is shown in terms of percent inhibition of the compound at varied concentrations.

Compound No.: The compound number shown in Examples.

TABLE 2

| Compound No. | Anti-C1 activity | | Inhibition of complement mediated hemolysis (%) | | |
|---|---|---|---|---|---|
| | $C\bar{1}r$ | $C\bar{1}s$ | $1 \times 10^{-5}$ | $1 \times 10^{-6}$ | $1 \times 10^{-7}$ |
| 1 | $2 \times 10^{-6}$ | $3 \times 10^{-6}$ | 100 | 99 | 75 |
| 2 | $1 \times 10^{-6}$ | $1 \times 10^{-6}$ | 100 | 100 | 91 |
| 3 | $7 \times 10^{-7}$ | $3 \times 10^{-7}$ | 100 | 100 | 99 |
| 4 | $2 \times 10^{-6}$ | $3 \times 10^{-7}$ | 100 | 100 | 59 |
| 5 | $1 \times 10^{-6}$ | $3 \times 10^{-7}$ | 100 | 100 | 96 |
| 6 | $5 \times 10^{-7}$ | $1 \times 10^{-6}$ | 100 | 100 | 100 |
| 7 | $1 \times 10^{-6}$ | $2 \times 10^{-6}$ | 100 | 100 | 98 |
| 8 | $8 \times 10^{-7}$ | $2 \times 10^{-6}$ | 100 | 100 | 98 |
| 9 | $4 \times 10^{-7}$ | $3 \times 10^{-6}$ | 100 | 100 | 94 |
| 10 | $5 \times 10^{-6}$ | $3 \times 10^{-7}$ | 100 | 100 | 91 |
| 11 | $5 \times 10^{-7}$ | $5 \times 10^{-7}$ | 100 | 100 | 43 |
| 12 | $1 \times 10^{-7}$ | $3 \times 10^{-7}$ | 100 | 100 | 93 |
| 14 | $7 \times 10^{-7}$ | $3 \times 10^{-7}$ | 100 | 100 | 28 |
| 15 | $3 \times 10^{-7}$ | $4 \times 10^{-7}$ | 100 | 100 | 99 |
| 16 | $4 \times 10^{-7}$ | $3 \times 10^{-7}$ | 100 | 100 | 97 |
| 17 | $5 \times 10^{-7}$ | $2 \times 10^{-6}$ | 100 | 100 | 93 |
| 18 | $3 \times 10^{-7}$ | $3 \times 10^{-6}$ | 100 | 100 | 97 |
| 19 | $2 \times 10^{-7}$ | $3 \times 10^{-7}$ | 97 | 97 | 93 |
| 20 | | | 100 | 98 | 43 |
| 23 | $3 \times 10^{-6}$ | $2 \times 10^{-6}$ | 100 | 95 | 76 |
| 25 | $1 \times 10^{-6}$ | $2 \times 10^{-6}$ | 100 | 98 | 82 |
| 26 | $5 \times 10^{-7}$ | $4 \times 10^{-6}$ | 100 | 98 | 93 |
| 28 | $2 \times 10^{-6}$ | $3 \times 10^{-6}$ | 100 | 82 | 35 |
| 31 | $2 \times 10^{-7}$ | $3 \times 10^{-7}$ | 100 | 98 | 97 |
| 33 | $7 \times 10^{-7}$ | $2 \times 10^{-6}$ | · 97 | 97 | 81 |
| 34 | $5 \times 10^{-7}$ | $5 \times 10^{-7}$ | 100 | 100 | 58 |
| 35 | $2 \times 10^{-6}$ | $3 \times 10^{-6}$ | 100 | 100 | 71 |
| 36 | $5 \times 10^{-7}$ | $4 \times 10^{-6}$ | 100 | 100 | 68 |
| 37 | $3 \times 10^{-6}$ | $4 \times 10^{-7}$ | 99 | 78 | 12 |
| 38 | $3 \times 10^{-7}$ | $3 \times 10^{-6}$ | 100 | 100 | 98 |
| 39 | $4 \times 10^{-7}$ | $4 \times 10^{-6}$ | 100 | 100 | 71 |

(2) Forssman shock:

The experiment was performed according to the method of I. G. Offerness et al. [Biochem. Pharmacol., 27 (14), 1873-1878 (1978)]. Male Hartlay guinea pig of about 300 g in body weight was used. Each guinea pig of the control group was administered intravenously with hemolysin (minimum dose to cause the shock) (commercial hemolysin, 5,000 U as assayed by the method of Ogata) and the time elapsed until death was observed. For the test group, each guinea pig was administered intravenously with hemolysin after the administration of test compound (3 mg/kg) and the time elapsed until death was observed. The results obtained were as shown in Table 3.

TABLE 3

| Control group (sec.) | Group administered with compound | |
|---|---|---|
| | Compound No. 1 | Compound No. 31 |
| 278 | Survival | Survival |
| 318 | Survival | Survival |
| 296 | Survival | Survival |

Method of administration

The present compound is most suitably administered orally, though can be administered by injection. It is used as a drug either alone or in combination with other drugs. It is administered generally in the form of medicinal composition, though can be administered as simple substance without any additive. Examples of medicinal composition include tablets, powders, capsules, syrups and solutions. An oral composition may contain common additives such as binders, diluents, lubricants, disintegrators and excipients. Oral solutions may be in the form of aqueous or oily suspension, solution, emulsion, syrup or elixir, or in the form of dry syrup which, before use, is readjusted with water or other suitable solvents. The solutions may contain common additives such as suspending agents, flavoring agents, diluents, or emulsifies. For injection, may be used aqueous suspensions or oily suspensions.

Dosage

The present compound may be administered to mammals (including man) orally at a dose of 10 to 200 mg per day or by intravenous injection at a dose of 1 to 20 mg per day. However, these doses are presented solely for the sake of example. A suitable dose for a patient should be determined depending upon the age and body weight of the patient and the features of illness.

Examples of pharmaceutical formulations are described below.

Examples of pharmaceutical formulations:

(1) Capsules:

| | |
|---|---|
| The present compound | 100.0 mg |
| Lactose | 59.0 |
| Crystalline cellulose | 33.4 |
| Calcium carboxymethylcellulose | 3.6 |
| Magnesium stearate | 4.0 |
| Total | 200.0 mg |

(2) Fine granules:

| | |
|---|---|
| The present compound | 50.0 mg |
| Lactose | 249.0 |
| Mannitol | 75.0 |
| Corn starch | 110.0 |
| Hydroxypropylcellulose | 16.0 |
| Total | 500.0 mg |

(3) Injections:

| | |
|---|---|
| The present compound | 5.0 mg |
| Water for injection | 2 ml |

Made up to injections in a customary manner.

Toxicity

The median lethal dose ($LD_{50}$) of the present compound is as shown in Table 4.

TABLE 4

| Compound | $LD_{50}$ mg/kg (mouse) | |
|---|---|---|
| No. | I.P. | P.O. |
| 1 | 100 | 2000 |
| 31 | 200 | 2500 |

Examples of preparation of the present compounds are described below. The physical data of each compound are summarized in Table 5.

TABLE 5

| Compound No. | $R_1$\N—(CH$_2$)$_n$—(A)—\$R_2$ | Salt | mp °C. | IR$\nu_{max}^{KBR}$ cm$^{-1}$ (—COO—) |
|---|---|---|---|---|
| 1 | HN\\>—NH—CH$_2$—furan\H$_2$N | 2MSA | 145 (d) | |
| 2 | CH$_3$—N\\>—NHCH$_2$—furan\CH$_3$—HN | 2MSA | 61 - (sinter) | 1720 |
| 3 | HN\\>—NH—furan\H$_2$N | 2MSA | 225–227 | |
| 4 | HN\\>—N(CH$_3$)—furan\H$_2$N | 2MSA | | 1730 |
| 5 | HN\\>—NH—furan\HN—CH$_3$ | 2HCl | 249–250 | |
| 6 | HN\\>—NHCH$_2$—furan\HN—CH$_3$ | HCL.MSA | 70 - (sinter) | 1720 |

TABLE 5-continued

| Compound No. | $R_1R_2N-(CH_2)_n-[A]-$ | Salt | mp °C. | IR $\nu_{max}^{KBR}$ cm$^{-1}$ (—COO—) |
|---|---|---|---|---|
| 7 | CH$_3$—N, C$_2$H$_5$—HN, =C—NHCH$_2$—furan | HCl.MSA | | 1730 |
| 8 | C$_2$H$_5$—N, C$_2$H$_5$—HN, =C—NHCH$_2$—furan | HCl.MSA | | 1730 |
| 9 | HN, H$_2$N, =C—NHCH$_2$CH$_2$—furan | HCl.MSA | | 1720 |
| 10 | 2-imidazolinyl-NH—furan | 2HCl | 212 (d) | 1715 |
| 11 | 2-imidazolinyl-NHCH$_2$—furan | 2MSA | 63 - (sinter) | 1730 |
| 12 | H$_3$CCONHCH$_2$—furan | MSA | 200–203 | |
| 13 | C$_{15}$H$_{31}$CONHCH$_2$—furan | HCl | 190–196 | |
| 14 | (CH$_3$)$_2$NCH$_2$CONHCH$_2$—furan | 2MSA | 70 - (sinter) | 1730 |
| 15 | HN=C(NH$_2$)—NH—C$_6$H$_4$—CONHCH$_2$—furan | 2MSA | 79 - (sinter) | 1720 |
| 16 | pyridyl-CONHCH$_2$—furan | 2MSA | 73 - (sinter) | 1730 |
| 17 | quinolinyl-CONHCH$_2$—furan | 2MSA | 68 - (sinter) | 1740 |
| 18 | C$_6$H$_5$—CH$_2$OCH$_2$CH$_2$CONHCH$_2$—furan | MSA | | 1730 |

TABLE 5-continued

| Compound No. | $R_1$<br>$\phantom{R}\diagdown$<br>N—(CH$_2$)$_n$—[A]—<br>$R_2$ | Salt | mp °C. | IR$\nu_{max}^{KBR}$ cm$^{-1}$ (—COO—) |
|---|---|---|---|---|
| 19 | C$_6$H$_5$—CH$_2$OCONHCH$_2$—(furan) | MSA | 180–183 | |
| 20 | C$_6$H$_5$—CH$_2$OCONHCH$_2$CH$_2$CONHCH$_2$—(furan) | MSA | 54–59 | 1700 |
| 21 | C$_6$H$_5$—CH$_2$OCONHCH$_2$—(cyclohexyl)—CONH—(furan) | MSA | 220–223 | |
| 22 | C$_6$H$_5$—CH$_2$OCONHCH$_2$—(cyclohexyl)—CONHCH$_2$—(furan) | MSA | | 1720 |
| 23 | (CH$_3$)$_2$NCH$_2$—(furan) | HCl.MSA | 217 (d) | |
| 24 | piperidinyl-N—CH$_2$—(furan) | HCl.MSA | 229–232 | |
| 25 | morpholinyl-N—CH$_2$—(furan) | HCl.MSA | 178–183 | |
| 26 | C$_6$H$_5$—CH$_2$—N(piperazinyl)N—CH$_2$—(furan) | 3TsOH | 198–202 | |
| 27 | C$_6$H$_5$—CH$_2$OCONHCH$_2$—(thiophene) | MSA | 192–194 (d) | |
| 28 | H$_2$N—C(=NH)—NHCH$_2$—(thiophene) | 2HCl | 181–184 | |
| 29 | (CH$_3$)$_3$COCONH—(benzofuran) | MSA | 215–218 (d) | |
| 30 | H$_2$N—C(=NH)—NH—(benzofuran) | 2MSA | 255–257 | |

TABLE 5-continued

| Compound No. | $R_1 \diagdown N-(CH_2)_n-\boxed{A}-$ $R_2 \diagup$ | Salt | mp °C. | IR$\nu_{max}^{KBR}$ cm$^{-1}$ (—COO—) |
|---|---|---|---|---|
| 31 | H₂NCH₂—⟨S⟩— | 2HBr | 272–274 (d) | |
| 32 | H₂N—⟨O⟩— | 2HCl | 110–113 | |
| 33 | H₂NCH₂—⟨O⟩— | 2HBr | 231–234 (d) | |
| 34 | H₂NCH₂CH₂CONHCH₂—⟨O⟩— | 2HBr | | 1700 |
| 35 | H₂N(CH₂)₄CHCONHCH₂—⟨O⟩— <br>                             \|<br>                             NH₂ | 3HBr | 118 - (sinter) | 1715 |
| 36 | Ph—CH₂OCH₂CHCONHCH₂—⟨O⟩— <br>                           \| <br>                          NH₂ | 2TFA | 137 - (sinter) | 1730 |
| 37 | H₂NCH₂—⟨cyclohexyl⟩—CONH—⟨O⟩— | MSA | 262 (d) | 1690 |
| 38 | H₂NCH₂—⟨cyclohexyl⟩—CONHCH₂—⟨O⟩— | 2HBr | 79 - (sinter) | 1725 |
| 39 | H₂NCH₂—⟨cyclohexyl⟩—CONHCH₂CH₂—⟨O⟩— | 2HBr | | 1730 |

MSA shows methanesulfonate.
TsOH shows toluenesulfonate.
TFA shows trifluoroacetate.

EXAMPLE 1

(Compound No. 1)

Synthesis of 6-amidino-2-naphthyl 5-guanidinomethyl-furan-2-carboxylate:

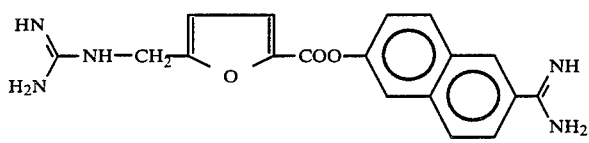

In a solvent mixture of 8 ml of dry N,N-dimethylformamide (DMF) and dry pyridine, were dissolved 2.0 g of 5-guanidinomethyl-furan-2-carboxylic acid methanesulfonate and 1.8 g of 6-amidino-2-naphthol methanesulfonate. To the resulting solution, while being cooled in ice, were added 1.8 g of DCC and a catalytic amount of 4-dimethylaminopyridine. The mixture was stirred for 30 minutes with cooling in ice and then overnight at 30° C. The insolubles were removed by filtration and ethyl ether was added to the filtrate. The supernatant was removed by decantation. The residue was dissolved in a small amount of methanol and the methanol solution was added dropwise to ethyl ether. After precipitation the supernatant was removed by decantation. These procedures were repeated twice. Finally, the precipitate was collected by filtration and dried to obtain 1.2 g of a pale yellow substance of 6-amidino-2-naphthyl 5-guanidinomethyl-furan-2-carboxylate dimethanesulfonate.

EXAMPLE 2

(Compound No. 2)

Synthesis of 6-amidino-2-naphthyl 5-(2,3-dimethyl)-guanidinomethyl-furan-2-carboxylate

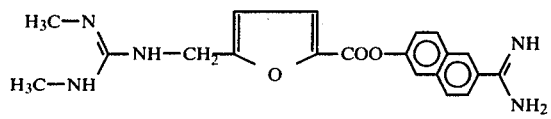

In a solvent mixture of 2 ml of DMF and 2 ml of pyridine were dissolved 500 mg of 5-(2,3-dimethyl)-guanidinomethyl-furan-2-carboxylic acid methanesulfonate, 360 mg of 6-amidino-2-naphthol methanesulfonate, 400 mg of DCC and a small amount of DMAP. The resulting solution was stirred overnight at room temperature. The insolubles were removed by filtration and ethyl ether was added to the filtrate. The resulting mixture was stirred. The precipitate was dissolved in a small amount of methanol and the methanol solution was added dropwise to ethyl acetate while stirring. The precipitate was collected by filtration to obtain 370 mg of 6-amidino-2-naphthyl 5-(2,3-dimetyl)guanidinomethylfuran-2-carboxylate dimethanesulfonate.

Compounds Nos. 3 to 30 were obtained as in Examples 1 and 2.

EXAMPLE 3

(Compound No. 31)

Synthesis of 6-amidino-2-naphthyl 5-aminomethyl-thiophene-2-carboxylate

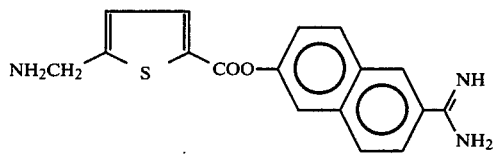

In 20 ml of a 30% HBr/acetic acid solution, was dissolved 1.0 g of 6-amidino-2-naphthyl 5-benzyloxycarbonylaminomethyl-thiophene-2-carboxylate methanesulfonate. The solution was stirred for 30 minutes at room temperature. Ethyl ether was added to the resulting solution. The precipitate was collected by filtration and recrystallized from a mixture of methanol and ethyl ether to obtain 800 mg of 6-amidino-2-naphthyl 5-aminomethyl-thiophene-2-carboxylate dihydrobromide.

Compounds Nos. 32 to 39 were obtained as in Example 3.

What is claimed is:

1. An amidino compound of formula (I)

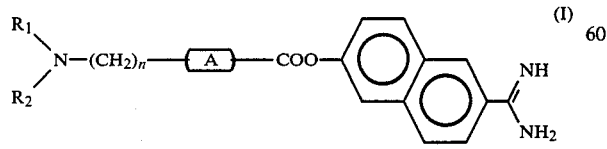

wherein A represents furan, thiophene or benzofuran; $R_1$ represents a hydrogen atom or a straight or branched chain alkyl group of 1 to 4 carbon atoms; $R_2$ represents a hydrogen atom, a straight or branched chain alkyl group of 1 to 4 carbon atoms, an acyl group or

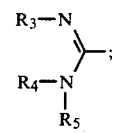

$R_3$, $R_4$ and $R_5$ represent a hydrogen atom or a straight or branched chain alkyl group of 1 to 4 carbon atoms; $R_1$ to $R_5$ taken together with the nitrogen atoms to which they are attached form a ring, which may optionally contain other hetero atoms; and n is 0, 1 or 2, and a pharmaceutically acceptable acid addition salt thereof.

2. An amidino compound and a pharmaceutically acceptable acid addition salt thereof according to claim 1, wherein $R_2$ is

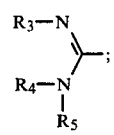

and $R_3$, $R_4$ and $R_5$ are a hydrogen atom or a straight or branched chain alkyl group of 1 to 4 carbon atoms.

3. An amidino compound and a pharmaceutically acceptable acid addition salt thereof according to claim 1, wherein the acyl group for $R_2$ is $R_6$—CO—, wherein $R_6$ represents a straight or branched chain alkyl group of 1 to 15 carbon atoms, a straight or branched chain alkoxy group of 1 to 4 carbon atoms, benzyloxy,

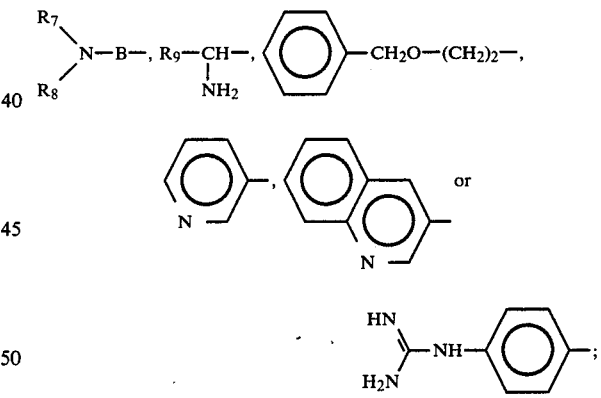

$R_7$ and $R_8$ represent a hydrogen atom, a straight or branched chain alkyl group of 1 to 4 carbon atoms or benzyloxycarbonyl; B represents —(CH$_2$)$_m$— or

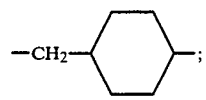

m is 1 or 2; and $R_9$ represents

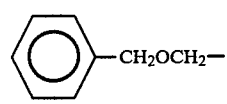

or
NH$_2$—(CH$_2$)$_4$—.

4. An amidino compound and a pharmaceutically acceptable acid addition salt thereof according to claim 1, wherein A is furan.

5. An amidino compound and a pharmaceutically acceptable acid addition salt thereof according to claim 2, wherein A is furan.

6. An amidino compound and a pharmaceutically acceptable acid addition salt thereof according to claim 3, wherein A is furan.

* * * * *